United States Patent [19]
Pichlmayr et al.

[11] Patent Number: 5,846,208
[45] Date of Patent: Dec. 8, 1998

[54] METHOD AND APPARATUS FOR THE EVALUATION OF EEG DATA

[75] Inventors: Ina Pichlmayr, Wedemark; Olaf Eckert, Hanover, both of Germany

[73] Assignee: Siemens Aktiengesellschaft, Munich, Germany

[21] Appl. No.: 916,398

[22] Filed: Aug. 22, 1997

[30] Foreign Application Priority Data

Sep. 4, 1996 [EP] European Pat. Off. .............. 96114153

[51] Int. Cl.$^6$ ............................................... A61B 5/0476
[52] U.S. Cl. ........................................................ 600/544
[58] Field of Search ..................................... 600/544, 545

[56] References Cited

U.S. PATENT DOCUMENTS 5,687,291  11/1997  Smyth .................................... 600/544
5,724,987   3/1998  Gevins et al. ......................... 600/544

FOREIGN PATENT DOCUMENTS

WO 95/33404  12/1995  WIPO .

OTHER PUBLICATIONS

"Predicting Depth of Anesthesia Using Bispectral Parameters in Neural Networks," Muthuswamy et al., Proceedings of the Annual International Conference of the IEEE Engineering in Medicine and Biology Society, Nov. 3–6, 1994, vol. 16, pp. 1787–1788.

"Autoregressive Modeling of EEG Signals for Monitoring Anesthetic Levels," Sharma et al., Proceedings of the 18th IEEE Annual Northeast Bioengineering Conference, Mar. 12–13, 1992, pp. 39–40.

"Monitoring of Anesthetic Level by EEG," Thomsen et al., Proceedings of the Ninth Annual Conference of the IEEE Engineering in Medicine and Biology Society, Nov. 13–16, 1987, vol. 3, pp. 1252–1253.

"Neural–Gas," Martinetz et al., IEEE Trans. on Neural Networks, vol. 4, No. 4, Jul., 1993, pp. 558–569.

"Was bringt die 3. Generation im Neuromonitoring für die klinishce Praxis?" Freye et al., Anästhesiolgie & Intensivmedizin, vol. 3, No. 37, 1996, pp. 120–127.

*Primary Examiner*—Scott M. Getzow
*Attorney, Agent, or Firm*—Hill & Simpson

[57] ABSTRACT

A method for the evaluation of EEG data for medical purposes includes the steps of acquiring EEG data, recognizing artifacts and determining an output data value with a neural network. In a training method for a neural network, training vectors are determined to which a respective data value is allocated, the neural network is trained with these training vectors, and an output data value is determined for each neuron that is based on the allocated data values of those training vectors that are contained in the data cluster represented by the neuron. A processing apparatus and an EEG monitor are configured for implementing the evaluation method for EEG data.

24 Claims, 7 Drawing Sheets

FIG.5

| Sub-network Designation | Number of Neurons | Power [μV²] | Median Frequency [Hz] |
|---|---|---|---|
| 1 | 13 | 0.0-5.0 | 0.0-2.0 |
| 2 | 14 | 5.0-10.0 | 0.0-2.0 |
| 3 | 9 | 10.0-25.0 | 0.0-2.0 |
| 4 | 8 | 25.0-50.0 | 0.0-2.0 |
| 5 | 2 | 50.0-75.0 | 0.0-2.0 |
| 6 | 2 | 75.0-2000.0 | 0.0-2.0 |
| 7 | 9 | 0.0-5.0 | 2.0-5.0 |
| 8 | 44 | 5.0-10.0 | 2.0-5.0 |
| 9 | 99 | 10.0-25.0 | 2.0-5.0 |
| 10 | 106 | 25.0-50.0 | 2.0-5.0 |
| 11 | 29 | 50.0-75.0 | 2.0-5.0 |
| 12 | 16 | 75.0-2000.0 | 2.0-5.0 |
| 13 | 6 | 0.0-5.0 | 5.0-10.0 |
| 14 | 36 | 5.0-10.0 | 5.0-10.0 |
| 15 | 178 | 10.0-25.0 | 5.0-10.0 |
| 16 | 186 | 25.0-50.0 | 5.0-10.0 |
| 17 | 56 | 50.0-75.0 | 5.0-10.0 |
| 18 | 27 | 75.0-2000.0 | 5.0-10.0 |
| 19 | 4 | 0.0-5.0 | 10.0-30.0 |
| 20 | 5 | 5.0-10.0 | 10.0-30.0 |
| 21 | 61 | 10.0-25.0 | 10.0-30.0 |
| 22 | 119 | 25.0-50.0 | 10.0-30.0 |
| 23 | 40 | 50.0-75.0 | 10.0-30.0 |
| 24 | 17 | 75.0-2000.0 | 10.0-30.0 |

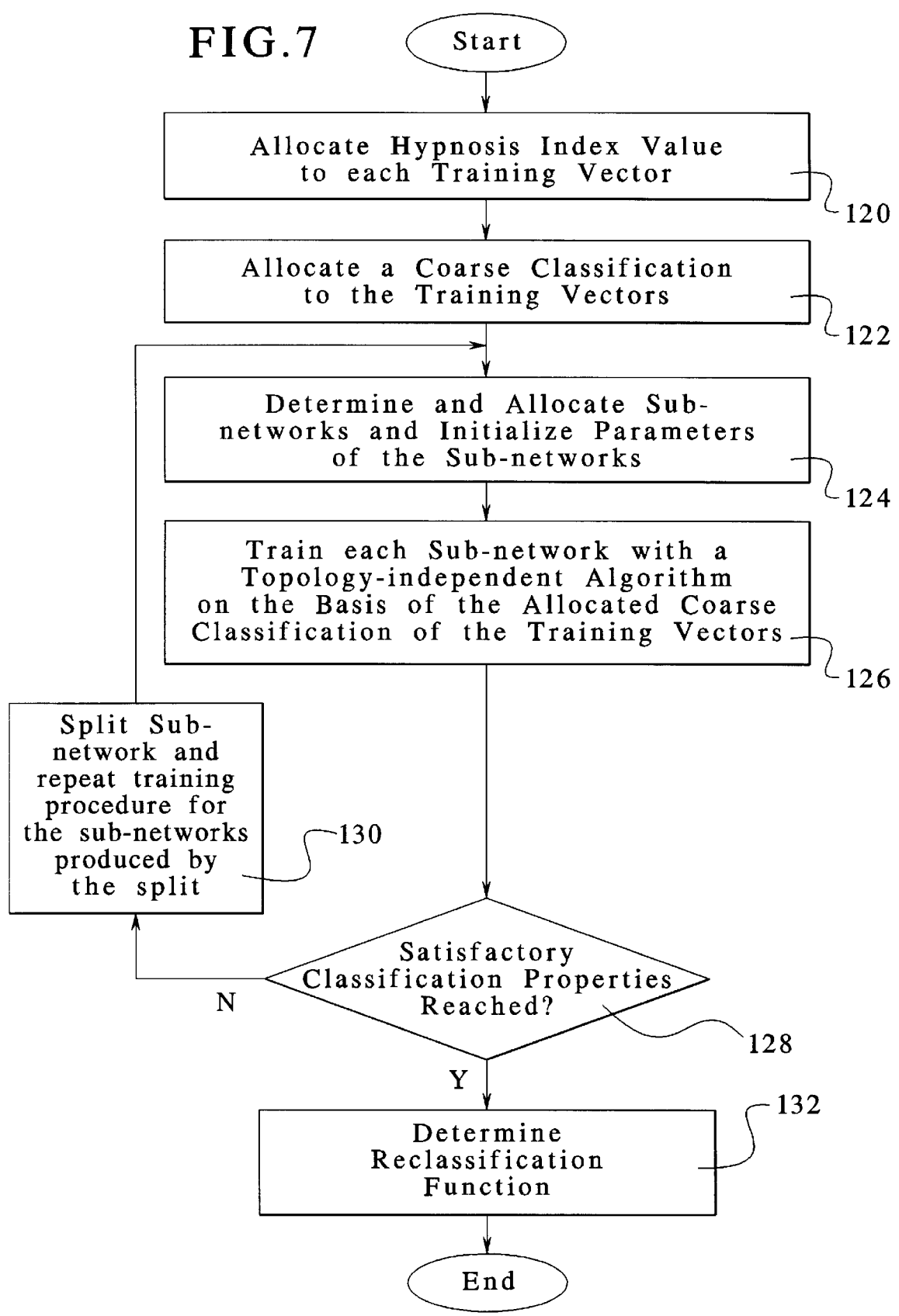

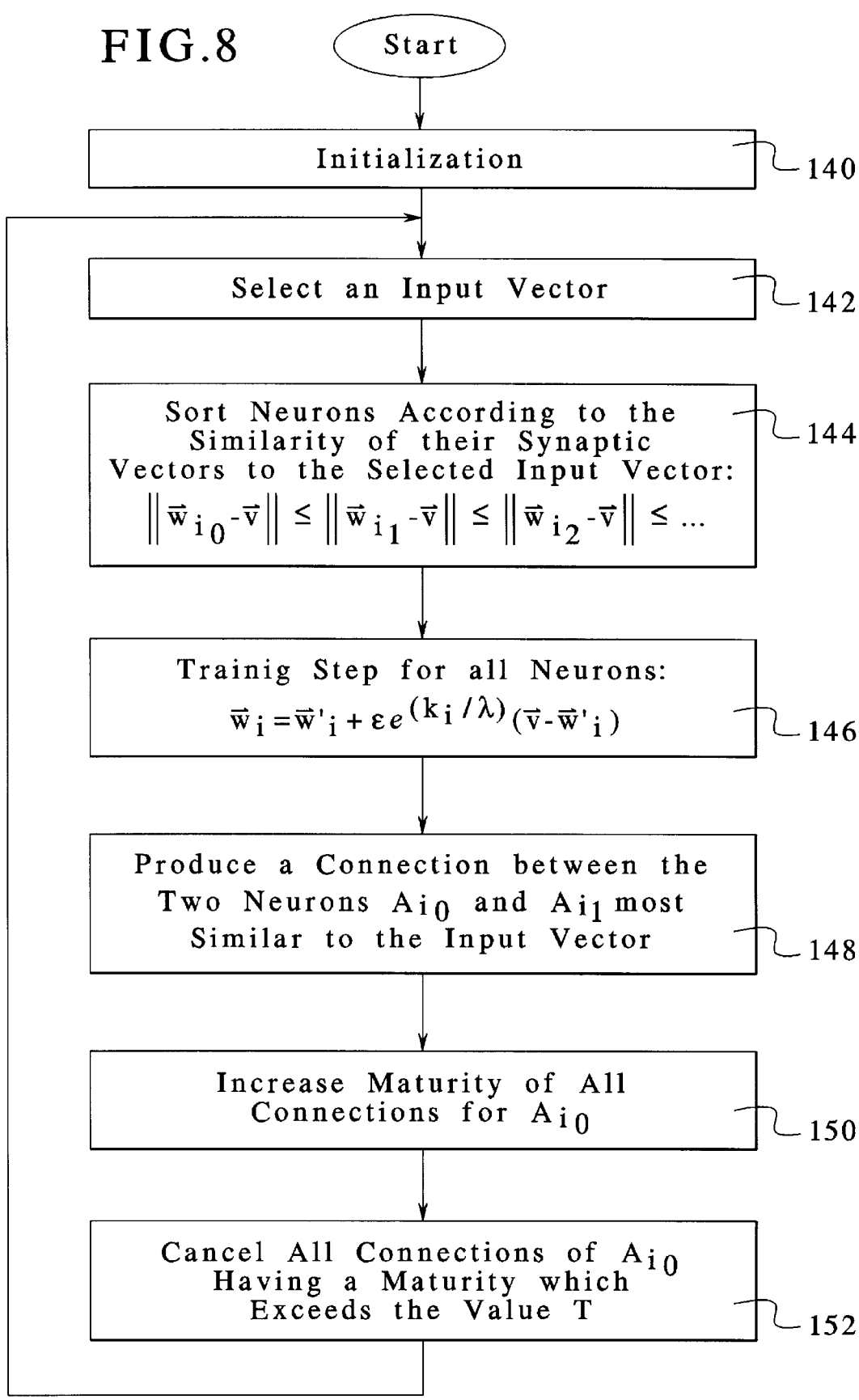

METHOD AND APPARATUS FOR THE EVALUATION OF EEG DATA

BACKGROUND OF THE INVENTION

1. Field of the Invention

The present invention is directed to a method and to an apparatus for the evaluation of electroencephalogram data (EEG data) for medical purposes, as well as to a method for training a neural network suitable for such an evaluation.

As used herein, "evaluation" means every method that generates a stream of output data from a stream of input data, the output data reflecting a specific, interesting aspect of the input data. In particular, the invention is employable for determining a hypnosis index from the EEG data. A "hypnosis index" is a value that indicate the depth of narcosis of a patient.

2. Description Of The Prior Art

The desire in current narcosis methods is to achieve a complete anaesthesia (freedom from pain) and hypnosis (sleeping state) of the patient with an optimally low medication dose. Since, however, the effectiveness and duration of the action of hynoptically acting medications differ from patient to patient and cannot be reliably predicted, it has been proposed to acquire the brain function with a measuring means during and after the narcosis.

The article "Was bringt die 3. Generation im Neuromonitoring fur die klinische Praxis?" von E. Freye, K. Grabitz and W. Sandman in the periodical "Anasthesiologie & Intensivmedizin" 3 (37), 1996, pages 120–127 contains an overview of devices for monitoring and evaluating EEG signals for determining the depth of narcosis. A spectral analysis of the EEG signals is implemented in these known devices. The parameters (power in predetermined frequency bands, spectral corner frequency, median frequency, etc.) are obtained as a result are optionally displayed and provide the physician with indications of the brain activity. In the device distributed under the registered trademark "Narkograph", a determination of the depth of narcosis also ensues which is graphically displayed on a picture screen.

The article by Jitendran Muthuswamy and Rob J. Roy "Predicting Depth of Anesthesia Using Bispectral Parameters in Neural Networks", which appeared in Proceedings of the Annual International Conference of the IEEE Engineering in medicine and Biology Society, Baltimore, Nov. 3.–6., 1994, Vol. 16, pp. 1787–1788, discloses a method for monitoring the depth of hypnosis using a neural network. The network is feedback-free and has three neural layers. It is trained by the method of "back-propagation". A "biocoherent index" as well as a MAC value determined from the bispectrum serve as input values for the network. In the classification of data sets, each data set applied to the network illicits specific activation degrees of all neurons of the network. A class of data sets is characterized by all members of the class producing activation degree of an output neuron which exhibits a predetermined value.

PCT publication WO 95/33404 discloses a method and a system for the evaluation of EEG data in order to determine a number of values, in particular a hypnosis index. EEG data are acquired and edited in this system. Sections of the EEG data falsified by artifacts are recognized. The value to be determined is generated from the EEG data on the basis of a predetermined calculating procedure. Different spectra are formed and statistical methods are applied. A neural network is not used.

The article by Ashutosh Sharma, Sarah E. Wilson and Rob J. Roy "Autoregressive Modeling of EEG Signals for Monitoring Anesthetic Levels", which appeared in Proceedings of the Eighteeth IEEE Annual Northeast Bioengineering Conference, march 12–13, 1992, pp. 39–40, discloses a method for determining a depth of hypnosis wherein the EEG data are first subjected to an auto-regression modeling. The auto-regression parameters determined in this way are interpreted by a feedback-free neural network having three layers. The network is trained by the method of "back-propagation". The network corresponds to that described in the article by Muthuswamy et al.

The article by Carsten Eckhart Thomsen, K. Norregaard-Christensen, A. Rosenfalck "Monitoring of Anesthetic Level by EEG", which appeared in Proceedings of the Ninth Annual Conference of the IEEE Engineering in Medicine and Biology Society, Nov. 13–16, 1987, Boston, Vol. 3 of 4, pp. 1252–1253, discloses a method for monitoring the depth of hypnosis wherein the EEG data are first subjected to an auto-regression modeling in order to acquire a feature vector. This feature vector is then allocated to one of several classes of hypnosis depth. The class division is determined during an initial training phase on the basis of a method of "non-monitored learning". A neural network is not utilized.

The problem continues to exist that the actual hypnosis state of a patient is difficult to measure and determined from EEG data. When an apparatus only displays the parameters obtained in the spectral analysis, these can only be interpreted by a specialist, who must expend a great deal of time. An indicated value of depth of narcosis, by contrast, does not always agree with the actual hypnotic state of the patient.

SUMMARY OF THE INVENTION

An object of the present invention is based to provide a method and an apparatus which allow acquisition of an interesting data value, for example a hypnosis index, from EEG data as reliably as possible.

The above object is achieved in accordance with the principles of the present invention in a method and apparatus for evaluating EEG data for medical purposes, particularly for determining a hypnosis index, wherein EEG data are acquired and edited, any sections of the EEG data which are falsified by artifacts are recognized, a feature vector is calculated from the edited EEG data as well as from information about the artifacts, and initial data value is determined with a neural network by allocating the feature vector to a data cluster represented by a neuron, and initial data value allocated to the data cluster then being determined, and an output data value is obtained from the initial data value and is made available, such as by presentation on a display.

As a result of the invention, an output data value that can be easily acquired is generated from the EEG data. When this is a hypnosis index, the depth of narcosis of a patient can be determined objectively and with great reliability. An unnecessarily high dosage of hypnotically acting medications is thereby avoided, allowing substantial cost savings can be achieved in the medication field and, moreover, the post-anesthetization and intensive care times can be shortened. An under-dosing is likewise prevented, which might cause the patient to consciously perceives parts of a surgical procedure. This is a traumatic experience for the patient, even when the he or she feels no pain. It is critical for recognizing such intra-operative waking states that the hypnotic component of the narcosis is acquired by the hypnosis index. By monitoring the hypnosis index, cerebral destruction and complication during the operation can also be recognized early.

In addition to monitoring narcosis during operations, the invention can also be utilized in intensive care of patients. An exact sedation setting of long-term patients is enabled, as a result of which the waking times, the intensive care days and the reconvalesence are shortened. Here, too, the brain function can be continuously monitored, and complications of the course of the intensive care (for example, sepsis that results in cerebral destruction) can be recognized.

A further field of employment of the invention is in vigilance monitoring of patients in psychiatry. The effective medications in cerebral treatments (for example, in arterial sclerosis) can be determined by the invention. Long-time monitoring is not required for this purpose. On the contrary, it suffices to compare the hypnosis index before and after the administration of the medication.

An important aspect of the inventive method is the reliable recognition of any sections of the EEG data which are falsified by artifacts. To that end, it is preferably provided that parameters of the EEG data be compared to statistically predetermined limit values and/or to smooth the parameter value. Preferably, only sections of the EEG data that are recognized as being artifact-free enter into the further interpretation. In an exemplary embodiment, the sections correspond to intervals having a duration of 2.0 s each that are referred to in the more detailed description below as "FFT intervals".

Feature vectors that include a number of components are classified by the neural network. Preferably, the signal power at predetermined frequency bands of the EEG data as well as further characteristic quantities of the EEG data enter into the feature vector. In order to be able to classify the feature vectors, the parameters of the neural network have been preferably determined by a training method wherein the network topology is not permanently prescribed or wherein the network topology can be changed during training. Especially good classification results are thus achieved.

The neural network preferably serves for the determination of a hypnosis index; however, the EEG data can also be evaluated in terms of other criteria and other indices can be determined.

The method for training the neural network is also a part of the invention. Parameters that implement a very reliable cluster analysis can be determined for networks with this method. The initial data set allocated to each training vector is preferably objectively determined by linear interpolation between permanently prescribed points.

In order to achieve good training results with comparatively slight calculating outlay, the network is preferably trained in separate sub-networks, each of which is allocated to a rough category of feature vectors. The sub-networks are preferably split during the course of the training procedure when no satisfactory cluster analysis can be achieved. The network can thus be perfected step-by-step.

The invention also includes a processing stage or EEG monitor with which the inventive analysis method can be implemented. The EEG monitor preferably displays the determined hypnosis index in a graduated presentation.

DESCRIPTION OF THE DRAWINGS

FIG. 5 is a table showing the rough classification of feature vectors produced in the inventive method and apparatus.

FIG. 7 is a flow chart of a training method for a neural network according to the preferred exemplary embodiment of the invention.

FIG. 8 is a flow chart of the training algorithm employed in the method shown in FIG. 7.

DESCRIPTION OF THE PREFERRED EMBODIMENTS

EEG Monitor And Evaluation Method

Figure 1:
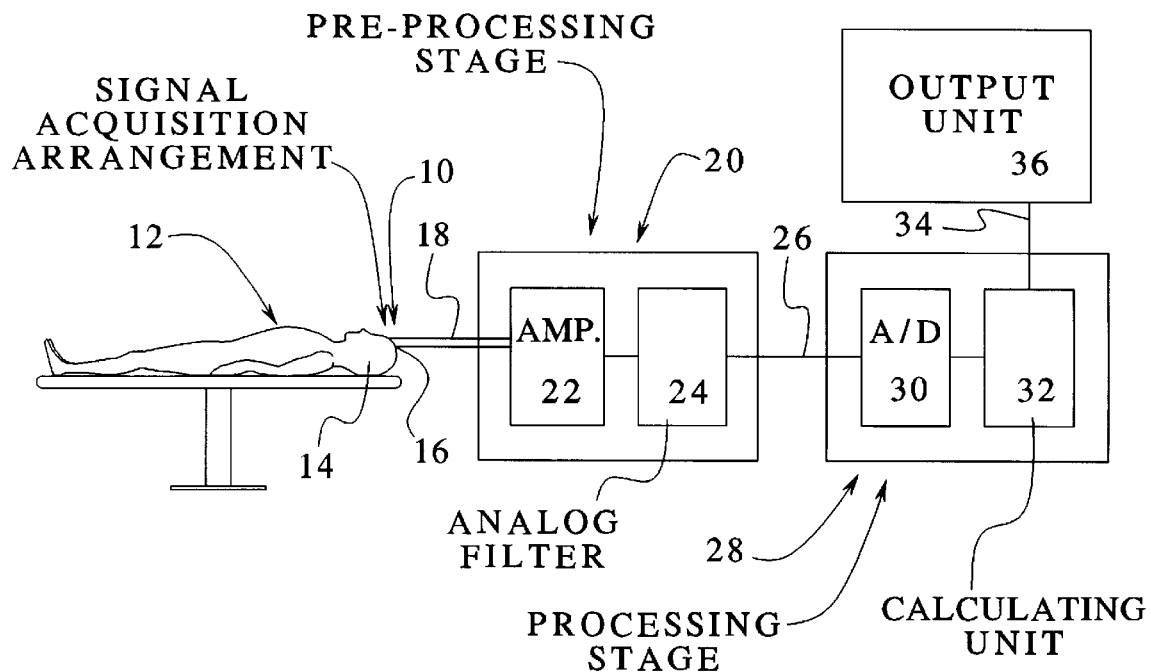
FIG. 1 is a schematic illustration of an inventive EEG monitor according to a preferred exemplary embodiment during operation.

The EEG monitor shown in FIG. 1 for determining a hypnosis index has a signal acquisition arrangement 10 for registering the electroencephalogram (EEG) of a patient 12. In the preferred embodiment, a bipolar potential between two positions at the head 14 of the patient 12 is measured by the signal acquisition arrangement 10. Two electrodes 16, which are fashioned as known Ag/AgCl sintered electrodes, are applied to the head 14 of the patient 12 with adhesive paste for this one-channel derivation. As an alternative, the signal acquisition arrangement 10 can be configured for a two-channel derivation, in which case it will then have four electrodes 16. Further, a ground electrode is applied to the forehead of the patient 12 in both types of derivation. Other numbers of electrodes are also possible.

The electrodes 16 are connected to a pre-processing stage 20 via a line 18. The line 18 is as short as possible in order to shorten the noise-susceptible distance for the unamplified raw signal deriving from the electrodes 16, which has an amplitude of only a few microvolts. The pre-processing stage 20 contains an amplifier unit 22 that transforms the raw signal to a signal on the order of magnitude of one volt. The amplifier unit 22 is connected to an analog filter 24 that exhibits a lower limit frequency of approximately 0.3 Hz and an upper limit frequency of approximately 40 Hz. The analog filter 24 eliminates, in particular, noise signal parts that are induced by the power network and exhibit a frequency of 50 Hz in Europe or 60 Hz in North America.

The analog filter 24 is connected via a line 26 to an analog-to-digital converter 30 that is contained in a processing stage 28. The processing stage 28 in the preferred exemplary embodiment is a standard IBM-compatible personal computer. The analog-to-digital converter 30 samples the input signal with 128 Hz and quantitizes it with a resolution of 12 bits. The resulting data stream is further-processed by a calculating unit 32 of the processing stage 22 in a number of steps. The processing procedure, presented in detail below, supplies result data, including a continuous hypnosis index. The result data are graphically edited by the processing stage 28 and are conducted via a line 34 to an output unit 36 fashioned as a picture screen and are displayed thereat.

Figure 2:
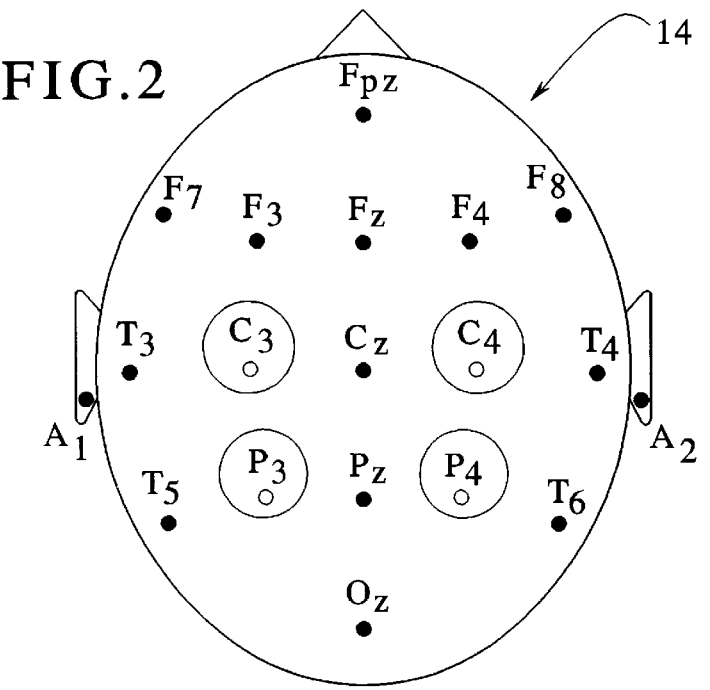
FIG. 2 is a schematic plan view onto a head of a patient with cap positions entered therein.

FIG. 2 schematically shows the internationally employed 10/20 system of electrode positions. Given the currently preferred type of one-channel derivation, the electrodes are applied at the positions $C_3$ and $P_3$. For the two-channel derivation, the bipolar potentials between the positions $C_3$ and $P_3$ are obtained for a first channel and between $C_4$ and $P_4$ are obtained for a second channel. The position for the ground electrode close to the forehead of the patient is not shown in FIG. 2.

Figure 3:
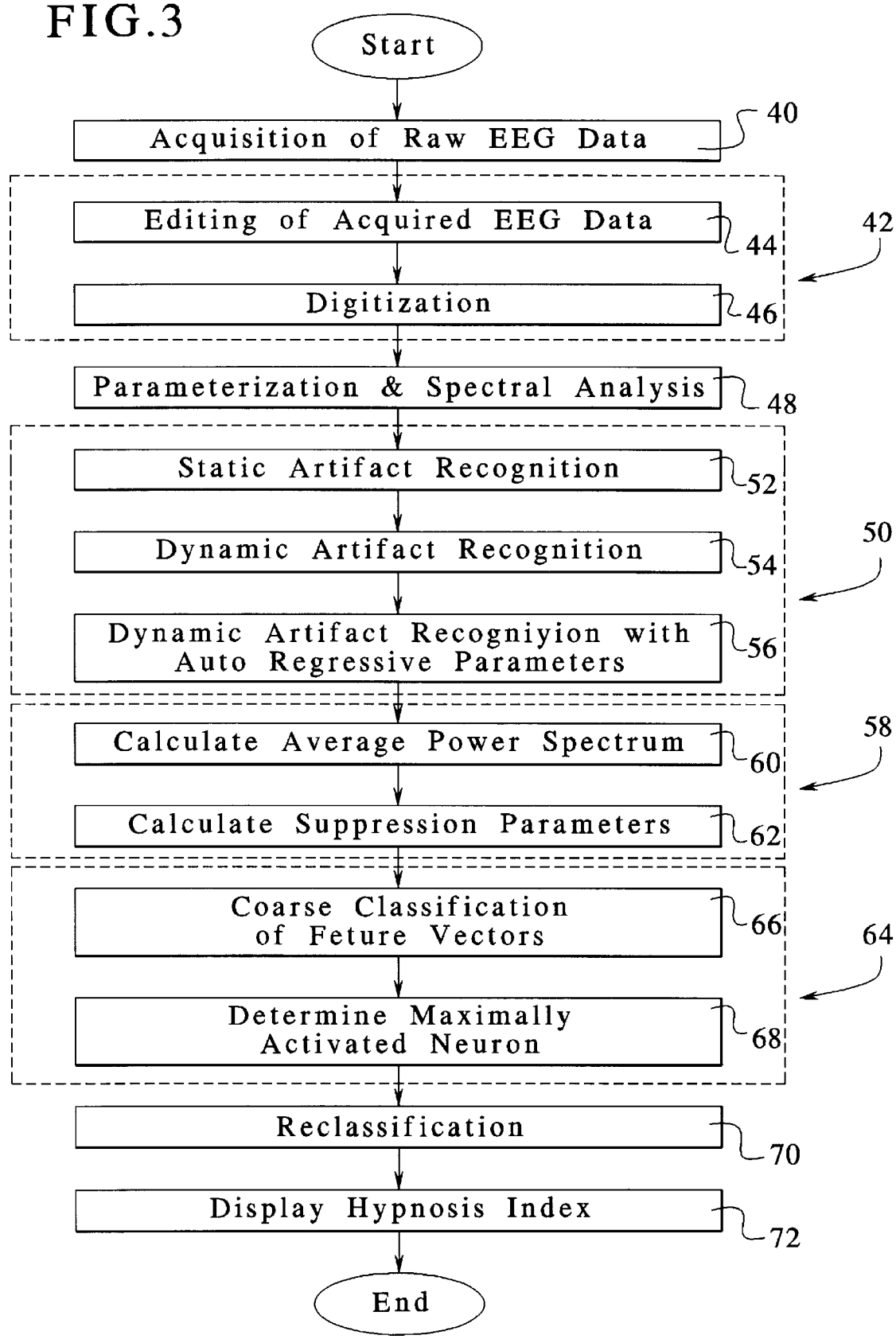
FIG. 3 is a flow chart of the analysis method according to the preferred exemplary embodiment of the invention.

FIG. 3 shows the inventive method for evaluating EEG data in the form of an overview, whereby a hypnosis index is determined. The following processing stages can be roughly separated.

1. Acquisition, editing and digitization of EEG data (Step 40, and steps 44 and 46 in block 42)
2. Parameterization of the digitized signal and spectral analysis (Step 48),
3. Recognition of artifacts (Block 50),
4. Calculation of the feature vector (Block 58),
5. Analysis by the neural network (Block 64),
6. Reclassification (Step 70), and
7. Presentation of the result value (Step 72).

Derivation, Editing and Digitization of EEG Data

The raw signals (Step 30) registered by the signal acquisition arrangement 10 are—as described above with reference to FIG. 1—edited by amplification and filtering in the pre-processing stage 20 (Step 44) and are digitized (Step 46) by the analog-to-digital converter 32. The digitized data are available to the processing stage 28 with a resolution of 12 bits and with a sampling frequency of 128 Hz.

Parameterization of the Digitized Signal and Spectral Analysis (Step 48)

From the digitized signal, the processing stage 28—using known algorithms—calculates a number of parameters for the later further processing.

To that end, the signal is first divided into blocks each having duration of 0.25 s (corresponding to 32 samples), FFT intervals each having a duration of 2.0 s (corresponding to 8 blocks or 256 samples) and evaluation intervals each having a duration of 30.0 s (corresponding to 120 blocks or 3840 samples).

The minimum and maximum sample, the average value, the variance (second moment) and higher moments are calculated for each block interval. Further, the coefficients a and b of a straight line approximating the signal curve during the block interval are determined with a linear regression analysis.

The aforementioned parameters as well as the maximum values of the first and second derivatives of the signal are also determined for each FFT interval. Moreover, the signal data of each FFT interval are subjected to a spectral analysis. In the exemplary embodiment described herein, a known algorithm for fast Fourier transformation (FFT algorithm) is implemented for this purpose, as described, for example, in the book "Einfuhrung in die Numerische Mathematik I" by Josef Stoer, 4th Edition, Springer Verlag 1983, Pages 71–81. A weighting in the FFT interval preferably ensues with a Hanning window.

As a result of the spectral analysis, the power spectrum of the signal is determined in the range from 0–63.5 Hz in 128 bands having 0.5 Hz each. Based on this power spectrum, a number of parameters is calculated for each FFT interval. In the preferred exemplary embodiment, these are, in detail:

Overall signal power,
Median frequency of the power spectrum (50% quantile),
Spectral corner frequency of the power spectrum (95% quantile),
Power of the $\delta$ band (0–3.0 Hz),
Power of the $\delta_1$ band (0–1.0 Hz),
Power of the $\delta_2$ band (1.5–2.0 Hz),
Power of the $\delta_3$ band (2.5–3.0 Hz),
Power of the $\theta$ band (3.5–7.0 Hz),
Power of the $\alpha$ band (7.5–12.0 Hz), and
Power of the $\beta$ band (12.5–30.0 Hz).

In addition, further parameters can be calculated, particularly power values of specific frequency bands.

Recognition of Artifacts (Block 50)

In order to avoid a falsification of the hypnosis index, it is important to recognize FFT intervals in which artifacts have occurred and to segregate them. Artifacts are temporary disturbances in the EEG signal that, for example, can arise due to electrical devices being turned on and off (in particular, high-frequency operation devices), due to movements on the part of the patient, given an intubation or due to poor electrical contacting.

A statistical artifact recognition (Step 52) ensues first in the preferred version of the method. The signal parameters determined in the above calculating step for each FFT interval are compared to permanently predetermined threshold or limit values. In detail, there are upper limits for the signal amplitude, the signal power, the first and second derivative of the signal and for parts of the power spectrum above 40 Hz. When a parameter exceeds the upper limit allocated to it, a disturbance due to an artifact is assumed. The signal variance, by contrast, cannot be permitted to fall below a predetermined lower limit.

In the next method step, a dynamic artifact recognition is implemented for a number of parameters (Steps 54 and 56). This has proven to be an especially effective means for the analysis of the EEG signal.

The basic principle of dynamic artifact recognition is to compare the current parameter value for a signal parameter to an exponentially smoothed parameter value. When the difference between a current and a smoothed parameter value exceeds a predetermined limit value in an FFD interval, then the FFD interval is marked as artifact-defective and is not utilized for the later calculation of the feature vector (in Block 58).

All parameters determined in Step 48 can be fundamentally utilized for the dynamic artifact recognition in Step 54. In the exemplary embodiment described herein, however, only the low-frequency bands of the power spectrum (bands $\delta_1$ through $\delta_3$) and, additionally, the first and the second derivatives of the EEG signal are employed. The previously determined, smoothed value is located in values. This value is updated in every FFT interval according to the equation $$\hat{p}_n = g \cdot p_n + (1-g) \cdot \hat{p}_{n-1}$$

wherein $P_n$ denotes the current parameter or signal value in the current ($n^{th}$) FFT interval $\hat{p}_n$ denotes the smooth value to be recalculated for the FFT interval and $\hat{p}_{n-1}$ denotes the previous, smooth value into which the FFT intervals up to the $(n-1)^{th}$ interval have entered. The extent to which the current value $P_n$ influences the smooth value $\hat{P}_n$ is determined by the permanently prescribed constant g (0<g<1).

As a further method step (Step 56), auto-regressive parameters are subjected to a dynamic artifact recognition according to the method described above with reference to Step 54. The auto-regressive parameters are the values $a_1$, $a_2$, ..., that have been estimated from the samples $X_1$ (i=1, ..., 256) of a FFT interval according to the equation $$x_n = a_1 \cdot x_{n-1} + a_2 \cdot x_{n-2} + \ldots$$

The estimation of auto-regressive parameters $a_1, a_2, \ldots$ is described in the book "Zeitreihenanalyse" by Rainer Schlittgen and Bernd H. J. Streitberg, 5th Edition, Oldenbourg Verlag 1994, pages 121–132.

Calculation Of The Feature Vector (Block 58)

Figure 4:
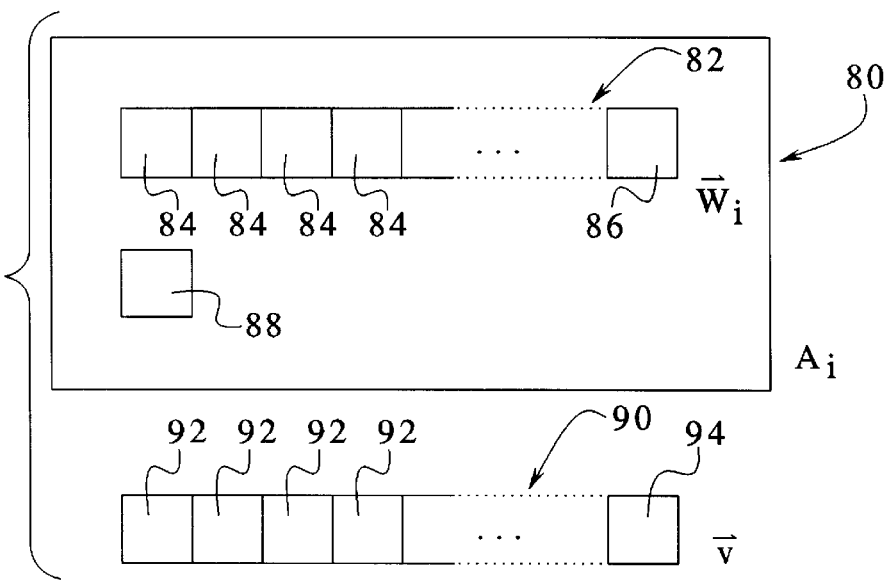
FIG. 4 is a schematic illustration of a neuron and of a feature vector produced in the inventive method and apparatus.

A feature vector v is calculated for every thirty-second evaluation interval, this being referenced 90 in FIG. 4. The feature vector 90 represents the input for the neural network. In the exemplary embodiment described, it has 21 components, namely 20 power components 92 and a suppression parameter component 94. The feature vector, however, can have a different number of components and different parameters as components. The power components 92 correspond to the power parts of the EEG signal on 20 frequency bands between 0 Hz and 30.0 Hz, with each frequency band being 1.5 Hz wide. The suppression character component 94 supplies a point of reference for the appearance of what is referred to as a burst suppression pattern in the EEG. A burst suppression pattern arises when the EEG has a baseline in sections that is irregularly interrupted by an activity having a higher amplitude.

For determining the power components 92 of the feature vector 90, an averaged power spectrum is calculated in Step 60. To that end, those individual spectra of the 15 individual spectra that were determined during the evaluation interval as a result of the spectral analyses are discarded for which (i.e. for whose FFT interval) the occurrence of an artifact had been found in Steps 52–56. The arithmetic average in the frequency range 0–30.0 Hz is formed from the remaining individual spectra. Three neighboring frequency bands of 0.5 Hz of each individual spectrum are thereby combined in order to determine the power values of the respectively 1.5 Hz wide frequency bands of the power components 92.

The suppression parameter component 94 of the feature vector 90 is determined in Step 62. This component indicates the percentage of block intervals (of 0.25 s each) in which the EEG line proceeded extremely flatly that occurred during the evaluation interval (30 s).

For recognition of a "flat" signal curve during a block interval, the results of the regression analysis for block intervals undertaken in Step 48 are used. A flat signal curve is assumed when the slope of the straight line approximating the signal curve during the block interval as well as the regression error (the scatter) do not exceed predetermined upper limits.

Analysis By Neural Network (Block 64)

The feature vector 90 generated in Steps 60 and 62 of block 58 is now subjected to a cluster analysis with a neural network. I.e., the feature vector 90 is investigated for its similarity to the number N of predetermined groups (clusters) of possible signal vectors. Each of the N groups corresponds to a neuron $A_i$ (i=1, . . . , N) of the neural network. N=1086 neurons are provided in the preferred exemplary embodiment. FIG. 4 shows a neuron $A_i$ referenced 80 that has a synaptic vector $w_i$ (referenced character 82). The synaptic vector 82 exhibits the same structure as the feature vector 90, namely 20 power components 84 and one suppression parameter component 86. In other words, all synaptic vectors 82 of the neurons 80 as well as the feature vectors 90 serving as input values of the neural network are elements of a vector space V. A norm $\|\cdot\|$ is permanently predetermined in the vector space V, namely the Euclidic Norm in the exemplary embodiment herein, this being defined by:

$$\|\vec{u}\| = \sum_{k=1}^{dimV} (u_k)^2$$

The designation dim V references the dimension of V (=number of components in u) and $u_k$ references the $k^{th}$ component u. For the exemplary embodiment described here, dim V=21 applies.

That neuron $A_i$ (referenced 80) of the network whose synaptic vector $w_i$ (referenced 82) is most similar to (closest to) the input feature vector v (referenced 90) is deemed maximally activated, i.e. for which the following is valid:

$$\|\vec{w} - \vec{v}\| = \min_{j = 1, \ldots, N} \|\vec{w_j} - \vec{v}\|$$

The determination of the maximally activated neuron 80 of the network ensues with the processing stage 28. Although it would be possible to successively determine the distance of the feature vector 90 from the synaptic vector 82 for all N neurons 80, a coarse classification of the feature vector 90 is undertaken first (Step 66) in the preferred exemplary embodiment, this determining a sub-network of the neural network.

According to the table shown in FIG. 5, the coarse classification (Step 66) ensues based on the overall signal power and on the median frequency that can be calculated from the power components 92 of the feature vector 90. A feature vector 90 is allocated to a sub-network when these parameters are contained within the interval limits recited in FIG. 5. In the exemplary embodiment described herein, one of 24 sub-networks that each contains between 2 and 186 neurons is determined as a result of the rough classification.

In the following Step 68, the feature vector 90 is compared to the synaptic vectors 82 of the neurons 80 of the identified sub-network in order to determine the maximally activated neuron 80 in the sub-network according to the above-recited equation.

The parameters of the neural network, i.e. the number N of the neurons in every sub-network, the criteria for coarse classification and the synaptic vector $w_i$ of each neuron 80 are permanently prescribed for the processing stage 28 and do not vary during operation. They are determined in a training process that is only implemented during the development of the system. This training process shall be described in detail below. Modified embodiments of the invention are possible, however, wherein a slow, further modification of the network parameters ensues during operation (see adaptive training).

Reclassification (Step 70)

As shown in FIG. 4, each neuron 80 of the network has an initial data value 88. The initial data value 88 of the maximally activated neuron for a feature vector 90 is the initial data value of the overall neural network and of the inventive system. In modified embodiments of the invention, the initial data value 88 is not directly allocated to the neuron 80 but only is derived during the course of further calculations.

Presentation of the Result Value (Step 72)

The determined initial data value 88, which indicates the current hypnosis index, is graphically edited by the processing stage 28 and is displayed by the output unit 36 fashioned as picture screen.

Figure 6:
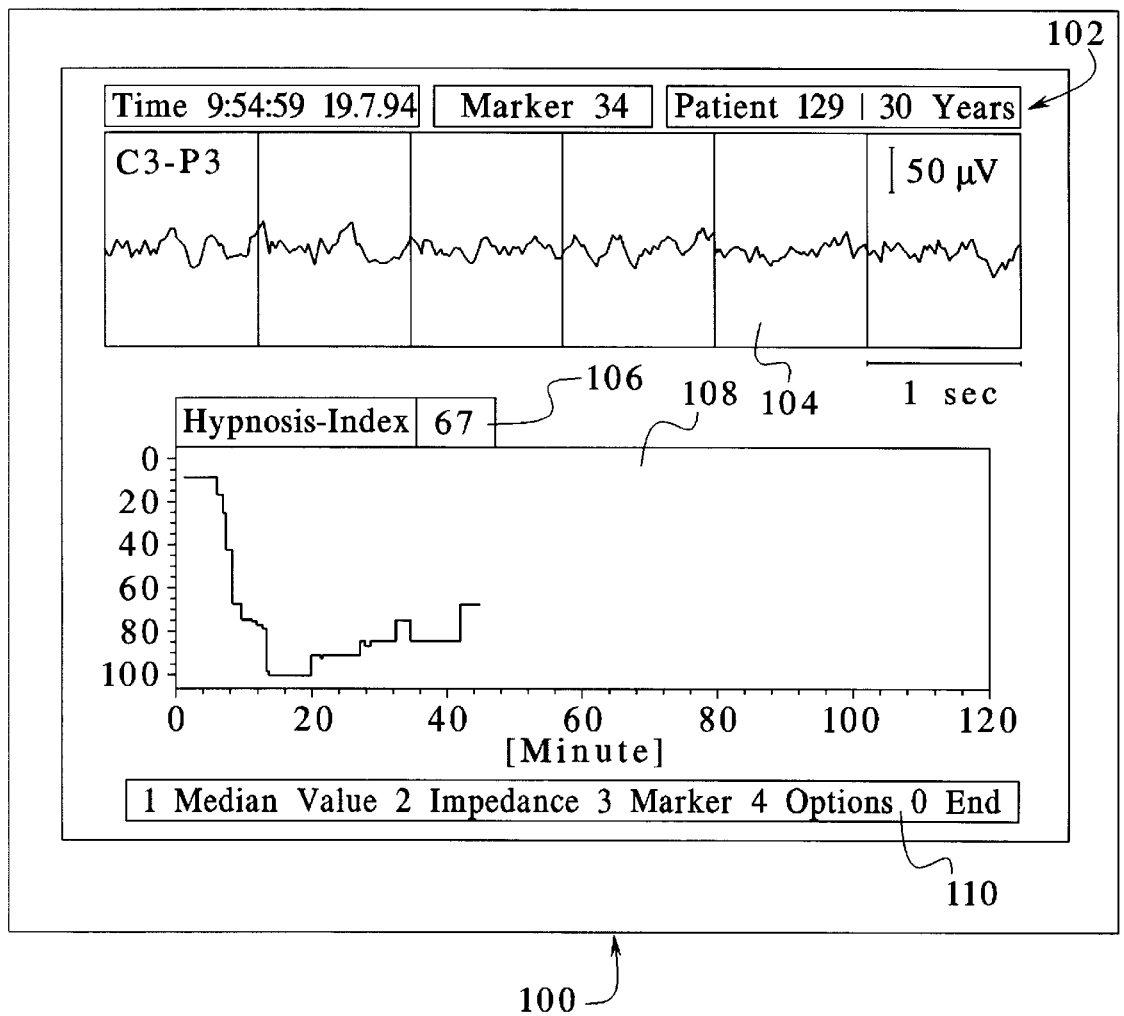
FIG. 6 is a view of the picture screen presentation displayed during the operation of the EEG monitor in accordance with the invention.

FIG. 6 shows an exemplary picture screen display 100 of a type that can occur during an operation. A head line 102 contains general data such as time of day, patient number and patient age. The EEG raw signal of the channel $C_3$-$P_3$ is displayed in an EEG window 104, this being updated every six seconds. An index display 106 numerically indicates the momentary value of the hypnosis index. The time course of the hypnosis index is shown as a curve in a window 108. A newly calculated index value of the curve is added at intervals of 30 seconds.

A function bar 110 enables control of the EEG monitor and of the display. For example, a graduated display of other parameter values (median frequency, corner frequency, etc.) or a display of the average power spectrum in the window 108 can be selected via the option 1.

Electrode impedances can be measured via the option 2. Consecutively numbered markings can be set with the option 3, these facilitating the allocation of clinically significant results in the retrospective consideration of a narcosis curve.

Further parameters such as blood pressure, heart beat rate, oxygen saturation and respiratory parameters can be supplied to the EEG monitor via an interface. These parameters are stored together with the EEG data and can likewise be displayed in the picture screen display 100.

Training Method

In the form of a flow chart, FIG. 7 shows the method implemented for training the neural network. In the preferred exemplary embodiment, the training is based on 192 complete narcosis initiations from which 25549 EEG sections of 30 seconds each have been determined. These EEG sections were converted into feature vectors (training vectors) in the method shown in FIG. 3 (Step 120).

A complete narcosis initiation proceeds from the waking state up to the first appearance of a burst suppression pattern. The hypnosis index value 0 was allocated to the waking state. Since the burst suppression pattern indicates a state of maximum hypnotic depth according to the generally recognized classification of Kugler ("Elektroenzephalographie in Klinik und Praxis", Suttgart-New York: Thieme 1981), this state was given the hypnosis index value of 100.

An allocated value of the hypnosis index was then determined for each training vector, this indicating what percentage of the time span between the start of infusion (hypnosis index 0) up to the first appearance of the burst suppression pattern (hypnosis index 100) had already elapsed in the narcosis initiation on which the training vector is based, when the training vector was registered (Step 120). In the training vectors, thus, the narcosis index drops linearly in the time course of the narcosis initiation.

A rough classification similar to the table shown in FIG. 5 was determined in Step 122. The number of neurons in the allocated sub-network and initialization parameters for the sub-networks were determined for each line of the table (Step 124).

The training algorithm shown in FIG. 8 and that is described in greater detail below was implemented in Step 126 for each sub-network determined in this way. A check (Step 128) was then made to determine whether the sub-network that was just trained had reached satisfactory classification properties. No neuron should be activated by two training vectors that correspond to highly different hypnosis index values. When a sub-network exhibited such neurons, i.e. when the training vectors classified too coarsely, this sub-network was split in two or more new sub-networks (Step 130) and the training procedure was repeated for these sub-networks.

When the desired classification sharpness was reached in all subnetworks then a reclassification function is determined (Step 132) that allocates an hypnosis index as output value to each neuron. This output value is the arithmetic average of the hypnosis index values of those training vectors that activate the neuron. Since the training was continued until each neuron was activated only by training vectors having relatively similar hypnosis index values (i.e. by a cluster of training vectors), the error caused by the averaging is slight.

The training algorithm (Step 126 in FIG. 7) employed for the training of the neural network in the exemplary embodiment of the invention described herein is presented in greater detail in FIG. 8. This algorithm is based on the "neural gas" algorithm presented in the article "'Neural-gas' network for vector quantization and its application to time-series prediction" by Thomas Martinetz, Stanislav Berkovich and Klaus Schulten in the periodical IEEE Transactions on Neural networks, Vol. 4, No. 4, July 1993, pages 558–569.

The basis of the training algorithm is a self-organizing neural network that is based on the principle of competing learning. The network is not bound to a predetermined topology, resulting in an especially good adaptation to complex pattern distributions being achieved. By contrast, other training algorithms are based on a predetermined neural topology, for example an arrangement of the In the training algorithm described below, a connection can exist between two respective neurons $A_i$ and $A_j$. This information required only during training is represented by auxiliary quantities $C_{ij}$ for all i, j,=1, ..., N. A value $C_{ij}=0$ states that the neurons $A_i$ and $A_j$ are not connected to one another, whereas a value $C_{ij}$ greater than 0 indicates an existing connection. Each connection exhibits a maturity presented by a natural number that is indicated by auxiliary quantities $t_{ij}$. According to the algorithm, the following operations are carried out.

(1) Initialization (Step 140):
  Allocates start values to all synaptic vectors $w_1$ for i=1, ... N, and
  set the coupling strengths $C_{ij}$ between all neurons to 0.

(2) Select an input vector v from the training vectors according to random principle (Step 142).

(3) Determine the number $k_i$ of neurons $A_j$ for each neuron $A_i$ for which the following is valid:

$$\|w_j - v\| \leq \|w_i - v\|.$$

For this purpose, the neurons $A_i$ are sorted according to the similarity of their synaptic vectors $w_i$ to the input vector v (Step 144):

$$\|w_{j_0} - v\| \leq \|w_{i_1} - v\| \leq \|w_{i_2} - v\| \leq \ldots$$

(4) Carry out a training step for all i=1, ..., N (Step 146):

$$w_i = w_i' + \epsilon e^{(k_i/\lambda)}(v - w_i')$$

$w_i$ is the value of $w_i$ before the implementation of the training step and $\epsilon$ and $\lambda$ are suitable constants.

(5) Connect the neurons $A_{i_0}$ and $A_{i_1}$ (Step 148):
  When $C_{i_0 i_1}=0$ then set $C_{i_0 i_1}>0$ and $t_{i_0 i_1}=0$
  When $C_{i_0 i_1}>0$ then and $t_{i_0 i_1}=0$.

(6) Increase the maturity of the connection of $A_{i_0}$ for all j=1, ..., N (Step 150):
  When $C_{i_0 j}>0$, then set $t_{i_0 j} t'_{i_0 j} 1$.

(7) Cancel those connections of the neurons $A_{i_0}$ for all j=1, ..., N whose maturity exceeds the value T (Step 152):
  When $C_{i_0 j} 22\ 0$ and $t_{i_0 j} T$, then set $C_{i_0 j}=0$.

(8) Continue at (2)

Experimental Results

In order to evaluate the dependability with which the EEG monitor according to the described exemplary embodiment of the invention can distinguish between the states "patient is awake" and "patient is adequately narcotic", EEG sections of 145 patients before the initiation of narcosis and five minutes after the intubation, i.e. in a condition of complete narcosis were investigated.

In the EEG sections in the waking state, the EEG monitor indicated a hypnosis index of at most 20% in 96.7% of the cases. A measurement of the In the EEG sections in the waking state, the EEG monitor indicated a hypnosis index of at most 20% in 96.7% of the cases. A measurement of the median frequency (separating value 6.0 Hz), by contrast, only supplied the correct result in 70.8% of the cases and a measurement of the corner frequency (separating value 19.5 Hz) supplied the correct result in only 68.9% of the cases.

Five minutes after the intubation, the EEG monitor likewise indicated a hypnosis index of at least 60% in 96.7% of the cases. Given the aboveindicated separating values, the measurement of the median frequency led to a correct result in 75.4% of the cases and the measurement of the corner frequency led to a correct result in 69.5% of the cases.

Figure 9A:
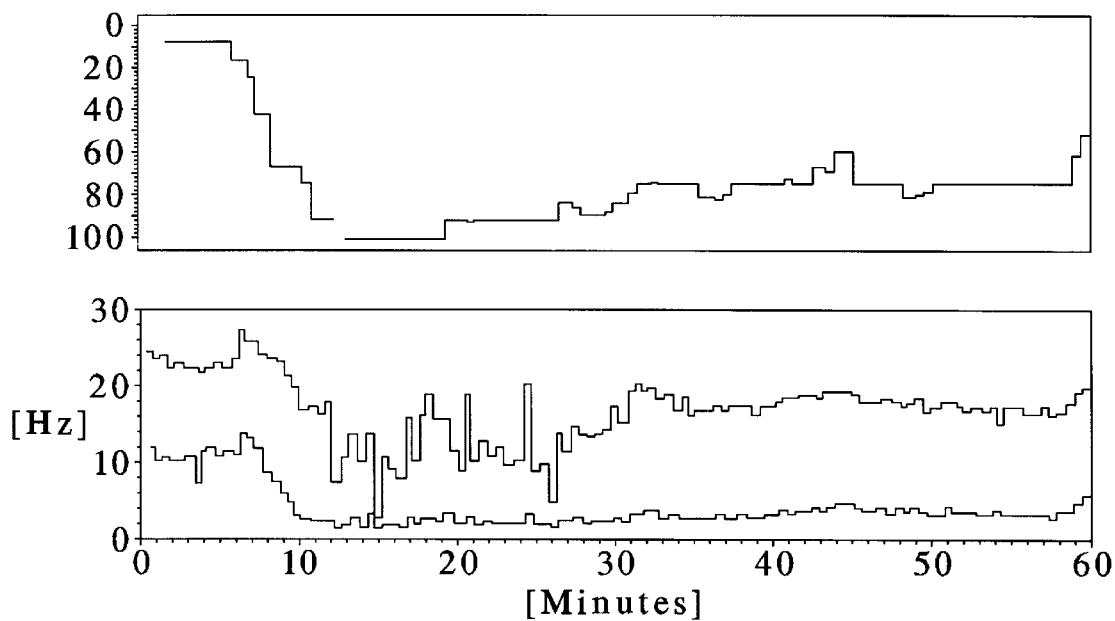
FIGS. 9a and 9b respectively show examples of the time curve of the hypnosis index in practical application.
Figure 9B:
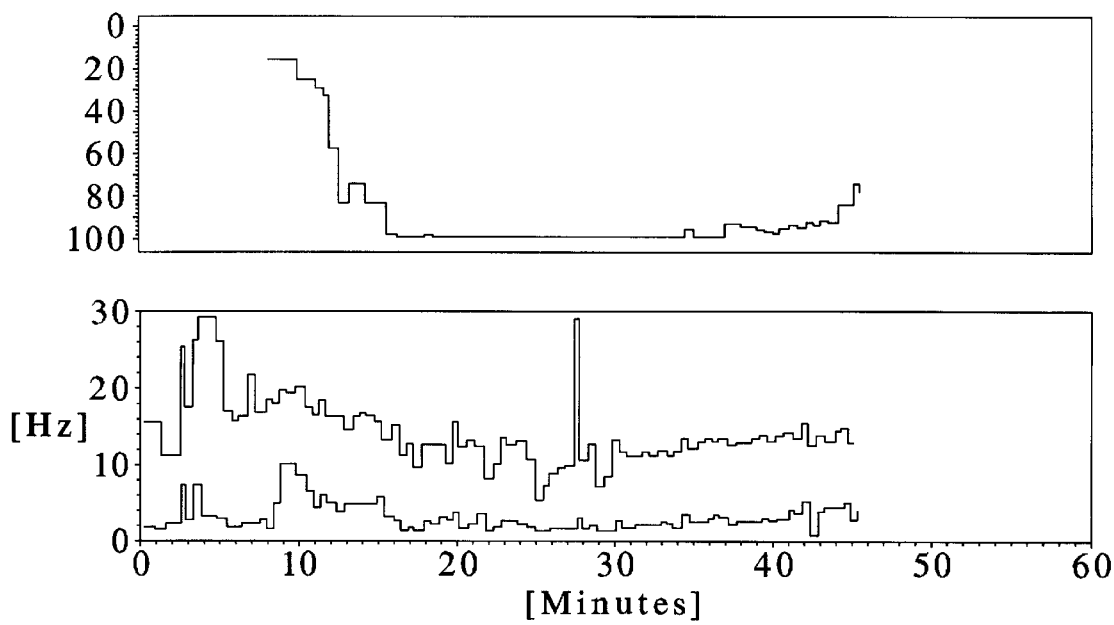

The time curve of the hypnosis index compared to the median frequency and the corner frequency is shown in FIG. 9a and FIG. 9b with reference to two exemplary cases. In both cases, the hypnosis index indicates the initiation of the narcosis with an approximately linear drop and the gradual spread of narcosis. By contrast, the median and corner frequency do not react linearly in the introductory phase of a narcosis, this making interpretation more difficult.

Given the example shown in FIG. 9a, in particular, the corner frequency is not a stable parameter. At a point in time of 45 minutes, the hypnosis index indicates a wake-up reaction given a cutaneous cut.

In the example shown at FIG. 9b, the corner frequency only reacts gradually to the introduction of narcosis.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for evaluating EEG data for medical purposes, comprising the steps of:
    (a) acquiring EEG data from a patient and editing said EEG data to produce edited EEG data;
    (b) identifying any sections of said EEG data falsified by artifacts and producing artifact information relating thereto;
    (c) calculating a feature vector from the edited EEG data and from said artifact information;
    (d) determining an initial data value in a neural network by allocating said feature vector to a data cluster represented by a neuron of said neural network, said initial data value being allocated to said data cluster; and
    (e) producing an output data value from said initial data value and displaying said output data value.

2. A method as claimed in claim 1 wherein step (a) comprises editing said EEG data by spectrally analyzing said EEG data acquired from said patient.

3. A method as claimed in claim 1 wherein step (b) comprises at least one of the steps of:
    comparing parameters of said EEG data to predetermined limit values and identifying a presence of an artifact if at least one of said predetermined limit values is exceeded by said parameters of said EEG data; and
    obtaining smoothed parameter values from previous EEG data and comparing said smoothed parameter values to current parameter values of said EEG data, and identifying a presence of an artifact in said EEG data if said current parameter values deviate from said smoothed parameter values by an amount exceeding a predetermined limit value.

4. A method as claimed in claim 3 comprising, in each comparing step, selecting power values of predetermined frequency bands of said EEG data as said parameters.

5. A method as claimed in claim 1 wherein step (c) comprises calculating a feature vector only from edited EEG data which has been identified in step (b) as not being falsified by artifacts.

6. A method as claimed in claim 1 wherein step (c) comprises at least one of the steps of:
    calculating components comprising said feature vector indicating a signal power in a predetermined frequency band of the edited EEG data during a measurement interval; and
    calculating at least one component indicating an appearance of a burst suppression pattern in said edited EEG data.

7. A method as claimed in claim 1 wherein step (d) comprises initially conducting a coarse classification of said feature vector in a first sub-network of said neural network for determining said data cluster allocated to said feature vector.

8. A method as claimed in claim 7 wherein the step of conducting said coarse classification comprises comparing parameters allocated to said feature vector to predetermined limit values.

9. A method as claimed in claim 1 wherein each neuron of said neural network has a synaptic vector associated therewith and wherein the step of allocating said feature vector to a data cluster represented by a neuron in step (d) comprises allocating a feature vector to a data cluster represented by a neuron of said neural network having a synaptic vector which is most similar to said feature vector.

10. A method as claimed in claim 1 wherein each neuron of said neural network has a parameter indicating an output data value for the data cluster represented by that neuron, and wherein step (e) comprises displaying said output data value for the data cluster represented by the neuron.

11. A method as claimed in claim 1 wherein each neuron of said neural network has a synaptic vector associated therewith, and comprising the additional step of determining parameters of said neural network, including said synaptic vectors, by a self-organizing training method.

12. A method as claimed in claim 11 wherein said neural network has a topology, and wherein the step of determining parameters of said neural network comprises determining parameters of said neural network by a self-organizing training method which is independent of said topology of said neural network.

13. A method as claimed in claim 1 wherein step (e) comprises determining a hypnosis index of said patient as said output data value.

14. A method for training neural network for evaluating EEG data for medical purposes, comprising the steps of:
    (a) determining a plurality of training vectors, each training vector having a data value allocated thereto;
    (b) determining initial parameters of a neural network;
    (c) conducting a training algorithm on said neural network including modifying said parameters of said neural network for allocating one neuron of said neural network to each cluster of training vectors; and
    (d) determining an output data value for each neuron dependent on the respective data values for all training vectors that are contained in the cluster of training vectors allocated to that neuron.

15. A method as claimed in claim 14 wherein step (d) is further defined by determining said output data value for a neuron by averaging the respective data values of all of said training vectors contained in the cluster of training vectors represented by that neuron.

16. A method as claimed in claim 14 wherein said neural network is free of any predetermined topology during steps (a), (b), (c) and (d).

17. A method as claimed in claim 16 comprising conducting training steps for each neuron according to the equation $$w_i = w'_i + \epsilon e^{(k_i/\lambda)}(v - w'_i)$$

wherein $w_i$ identifies a value of a synaptic vector of a neuron after conducting a training step, $w'_i$ is a value of a synaptic vector before conducting a training step, v is a training vector, $k_i$ is a number of neurons whose synaptic vectors are more similar to the training vector than the synaptic vector $w'_i$ and $\epsilon$ and $\lambda$ are predetermined constants.

18. A method as claimed in claim 14 comprising initially conducting a coarse classification of said training vectors among a number of coarses categories and respectively allocating different sub-networks of said neural network to each coarse category of training vectors, each sub-network then being trained only with the training vectors contained in the coarse category allocated to that sub-network.

19. A method as claimed in claim 18 comprising splitting a coarse category of training vectors if no satisfactory classification results can be obtained for all training vectors in said coarse category.

20. A processor for training neural network for evaluating EEG data for medical purposes, comprising:

means for determining a plurality of training vectors, each training vector having a data value allocated thereto;

means for determining initial parameters of a neural network;

means for conducting a training algorithm on said neural network including modifying said parameters of said neural network for allocating one neuron of said neural network to each cluster of training vectors; and means for determining an output data value for each neuron dependent on the respective data values for all training vectors that are contained in the cluster of training vectors allocated to that neuron.

21. An EEG apparatus comprising:

means for acquiring EEG data from a patient and editing said EEG data to produce edited EEG data;

means for identifying any sections of said EEG data falsified by artifacts and producing artifact information relating thereto;

means for calculating a feature vector from the edited EEG data and from said artifact information;

means for determining an initial data value in a neural network by allocating said feature vector to a data cluster represented by a neuron of said neural network, said initial data value being allocated to said data cluster; and means for producing an output data value from said initial data value and displaying said output data value.

22. An EEG apparatus as claimed in claim 21 wherein said means for displaying comprises means for displaying momentary output data values.

23. An EEG apparatus as claimed in claim 21 wherein said means for displaying comprises means for displaying continuously updated and graduated output data values.

24. An EEG monitor as claimed in claim 21 wherein said means for producing an output value comprises means for producing a hypnosis index and for displaying said hypnosis index.

* * * * *